(12) United States Patent
Henderson et al.

(10) Patent No.: US 7,806,922 B2
(45) Date of Patent: Oct. 5, 2010

(54) SINTERED RING SUPPORTED VASCULAR GRAFT

(75) Inventors: Jamie Henderson, Oakland, NJ (US); Dennis Kujawski, Warwick, NY (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 0 days.

(21) Appl. No.: 11/026,748

(22) Filed: Dec. 31, 2004

(65) Prior Publication Data

US 2006/0149361 A1      Jul. 6, 2006

(51) Int. Cl.
*A61F 2/06* (2006.01)
(52) U.S. Cl. .................................................. 623/1.25
(58) Field of Classification Search .......... 623/1.1–1.25
See application file for complete search history.

(56) References Cited

U.S. PATENT DOCUMENTS

| | | | |
|---|---|---|---|
| 3,640,984 A * | 2/1972 | Miller | 428/402 |
| 3,664,915 A | 5/1972 | Gore | |
| 3,953,566 A * | 4/1976 | Gore | 264/505 |
| 3,962,153 A | 6/1976 | Gore | |
| 4,096,227 A | 6/1978 | Gore | |
| 4,101,984 A | 7/1978 | MacGregor | |
| 4,187,390 A | 2/1980 | Gore | |
| 4,208,745 A | 6/1980 | Okita | |
| 4,280,500 A | 7/1981 | Ono | |
| 4,281,669 A | 8/1981 | MacGregor | |
| 4,304,010 A | 12/1981 | Mano | |
| 4,355,426 A | 10/1982 | MacGregor | |
| 4,454,249 A | 6/1984 | Suzuki et al. | |
| 4,459,252 A | 7/1984 | MacGregor | |
| 4,576,608 A | 3/1986 | Homsy | |
| 4,627,836 A | 12/1986 | MacGregor | |
| 4,647,416 A * | 3/1987 | Seiler et al. | 264/118 |
| 4,713,070 A | 12/1987 | Mano | |
| 4,743,480 A | 5/1988 | Campbell et al. | |

(Continued)

FOREIGN PATENT DOCUMENTS

CA       1069252       1/1980

(Continued)

OTHER PUBLICATIONS

PCT Notification of Transmittal of the International Search Report and the Written Opinion of the International Searching Authority, or the Declaration for International Application No. PCT/US2005/047252, May 17, 2006 (2 pages).

(Continued)

*Primary Examiner*—David Isabella
*Assistant Examiner*—Ann Schillinger
(74) *Attorney, Agent, or Firm*—Vidas, Arrett & Steinkraus P.A.

(57) ABSTRACT

The vascular graft includes a PTFE tube having non-expanded portions formed from sintering a PTFE green tube extrudate. The non-expanded portions are distributed longitudinally along the PTFE tube. The PTFE tube also has expanded portions formed subsequent to the sintering of the PTFE green tube extrudate. The expanded and non-expanded portions are integral with one another, and alternate with one another along the length of the PTFE tube. The expanded and non-expanded portions each have a respective stiffness, where the stiffness of the non-expanded portion is greater than that of the expanded portion.

12 Claims, 7 Drawing Sheets

U.S. PATENT DOCUMENTS

| | | | |
|---|---|---|---|
| 4,816,339 A | 3/1989 | Tu et al. | |
| 4,822,341 A | 4/1989 | Colone et al. | |
| 4,849,285 A | 7/1989 | Dillon | |
| 4,902,423 A | 2/1990 | Bacino | |
| 4,957,669 A | 9/1990 | Primm | |
| 4,973,609 A | 11/1990 | Browne | |
| 4,975,669 A | 12/1990 | Wojtowicz | |
| 5,024,671 A * | 6/1991 | Tu et al. | 623/1.54 |
| 5,071,609 A | 12/1991 | Tu et al. | |
| 5,141,522 A | 8/1992 | Landi | |
| 5,169,597 A | 12/1992 | Davidson | |
| 5,192,310 A | 3/1993 | Herweck et al. | |
| 5,207,960 A | 5/1993 | Moret de Rocheprise | |
| 5,210,947 A | 5/1993 | Donnelly et al. | |
| 5,326,355 A | 7/1994 | Landi | |
| 5,433,909 A | 7/1995 | Martakos et al. | |
| 5,449,373 A | 9/1995 | Pinchasik et al. | |
| 5,462,781 A | 10/1995 | Zukowski | |
| 5,477,864 A | 12/1995 | Davidson | |
| 5,509,933 A | 4/1996 | Davidson et al. | |
| 5,607,478 A * | 3/1997 | Lentz et al. | 623/23.69 |
| 5,609,624 A * | 3/1997 | Kalis | 623/1.32 |
| 5,620,763 A | 4/1997 | House et al. | |
| 5,628,786 A * | 5/1997 | Banas et al. | 623/1.13 |
| 5,641,373 A | 6/1997 | Shannon et al. | |
| 5,643,309 A * | 7/1997 | Myler et al. | 623/1.15 |
| 5,716,660 A | 2/1998 | Weadock et al. | |
| 5,718,973 A | 2/1998 | Lewis et al. | |
| 5,733,303 A | 3/1998 | Israel et al. | |
| 5,735,892 A | 4/1998 | Myers et al. | |
| 5,747,128 A * | 5/1998 | Campbell et al. | 428/35.7 |
| 5,749,880 A | 5/1998 | Banas et al. | |
| 5,782,910 A | 7/1998 | Davidson | |
| 5,800,512 A | 9/1998 | Lentz et al. | |
| 5,810,870 A | 9/1998 | Myers et al. | |
| 5,824,042 A * | 10/1998 | Lombardi et al. | 623/1.13 |
| 5,824,050 A * | 10/1998 | Karwoski et al. | 623/1.4 |
| 5,840,775 A | 11/1998 | Howard, Jr. et al. | |
| 5,843,171 A * | 12/1998 | Campbell et al. | 606/198 |
| 5,843,173 A | 12/1998 | Shannon et al. | |
| 5,858,556 A | 1/1999 | Eckert et al. | |
| 5,861,033 A * | 1/1999 | Martakos et al. | 623/1.1 |
| 5,897,587 A | 4/1999 | Martakos et al. | |
| 5,925,075 A | 7/1999 | Myers et al. | |
| 5,928,279 A * | 7/1999 | Shannon et al. | 623/1.13 |
| 5,972,018 A * | 10/1999 | Israel et al. | 606/198 |
| 5,976,192 A * | 11/1999 | McIntyre et al. | 600/36 |
| 5,980,799 A * | 11/1999 | Martakos et al. | 264/127 |
| 6,001,125 A * | 12/1999 | Golds et al. | 623/23.7 |
| 6,004,348 A * | 12/1999 | Banas et al. | 623/23.7 |
| 6,010,529 A | 1/2000 | Herweck et al. | |
| 6,016,848 A * | 1/2000 | Egres, Jr. | 138/137 |
| 6,039,755 A | 3/2000 | Banas et al. | |
| 6,048,360 A * | 4/2000 | Khosravi et al. | 623/1.11 |
| 6,048,484 A | 4/2000 | House et al. | |
| 6,053,943 A * | 4/2000 | Edwin et al. | 623/1.25 |
| 6,063,112 A * | 5/2000 | Sgro | 623/1.12 |
| 6,080,198 A | 6/2000 | Lentz et al. | |
| 6,124,523 A * | 9/2000 | Banas et al. | 623/1.15 |
| 6,132,457 A | 10/2000 | Chobotov | |
| 6,143,022 A | 11/2000 | Shull et al. | |
| 6,146,414 A * | 11/2000 | Gelman | 623/1.23 |
| 6,187,054 B1 * | 2/2001 | Colone et al. | 128/898 |
| 6,203,735 B1 | 3/2001 | Edwin et al. | |
| 6,214,039 B1 * | 4/2001 | Banas et al. | 623/1.13 |
| 6,231,598 B1 * | 5/2001 | Berry et al. | 623/1.15 |
| 6,245,101 B1 * | 6/2001 | Drasler et al. | 623/1.15 |
| 6,264,684 B1 * | 7/2001 | Banas et al. | 623/1.13 |
| 6,267,834 B1 | 7/2001 | Shannon et al. | |
| 6,283,991 B1 * | 9/2001 | Cox et al. | 623/1.13 |
| 6,287,337 B1 | 9/2001 | Martakos et al. | |
| 6,306,162 B1 | 10/2001 | Patel | |
| 6,319,279 B1 | 11/2001 | Shannon et al. | |
| 6,334,867 B1 * | 1/2002 | Anson | 623/1.13 |
| 6,355,063 B1 | 3/2002 | Calcote | |
| 6,364,900 B1 * | 4/2002 | Heuser | 623/1.11 |
| 6,371,981 B1 * | 4/2002 | Yang et al. | 623/1.13 |
| 6,383,214 B1 | 5/2002 | Banas et al. | |
| 6,402,779 B1 * | 6/2002 | Colone et al. | 623/1.49 |
| 6,416,537 B1 | 7/2002 | Martakos et al. | |
| 6,428,571 B1 * | 8/2002 | Lentz et al. | 623/1.4 |
| 6,443,981 B1 | 9/2002 | Colone et al. | |
| 6,451,047 B2 * | 9/2002 | McCrea et al. | 623/1.13 |
| 6,458,152 B1 | 10/2002 | Khosravi et al. | |
| 6,464,720 B2 * | 10/2002 | Boatman et al. | 623/1.15 |
| 6,488,701 B1 | 12/2002 | Nolting et al. | |
| 6,572,648 B1 | 6/2003 | Klumb et al. | |
| 6,579,314 B1 * | 6/2003 | Lombardi et al. | 623/1.44 |
| 6,582,463 B1 | 6/2003 | Mowry et al. | |
| 6,605,119 B1 | 8/2003 | Colone et al. | |
| 6,699,276 B2 | 3/2004 | Sogard et al. | |
| 6,719,783 B2 | 4/2004 | Lentz et al. | |
| 6,758,858 B2 | 7/2004 | McCrea et al. | |
| 6,786,920 B2 | 9/2004 | Shannon et al. | |
| 6,790,225 B1 | 9/2004 | Shannon et al. | |
| 6,797,217 B2 | 9/2004 | McCrea et al. | |
| 6,805,706 B2 * | 10/2004 | Solovay et al. | 623/1.15 |
| 6,994,723 B1 * | 2/2006 | McMahon | 623/1.49 |
| 7,011,682 B2 * | 3/2006 | Lashinski et al. | 623/2.37 |
| 7,090,693 B1 * | 8/2006 | Chobotov et al. | 623/1.13 |
| 2001/0010344 A1 * | 8/2001 | Fitzpatrick | 242/439.3 |
| 2001/0020181 A1 * | 9/2001 | Layne | 623/1.13 |
| 2001/0021870 A1 | 9/2001 | Banas et al. | |
| 2001/0025131 A1 | 9/2001 | Banas et al. | |
| 2002/0026231 A1 | 2/2002 | Shannon | |
| 2002/0042645 A1 | 4/2002 | Shannon | |
| 2002/0052649 A1 | 5/2002 | Greenhalgh | |
| 2002/0111667 A1 * | 8/2002 | Girton et al. | 623/1.13 |
| 2002/0115986 A1 * | 8/2002 | Shadduck | 604/891.1 |
| 2002/0198588 A1 | 12/2002 | Armstrong et al. | |
| 2003/0017775 A1 * | 1/2003 | Sowinski et al. | 442/315 |
| 2003/0028240 A1 | 2/2003 | Nolting et al. | |
| 2003/0135265 A1 * | 7/2003 | Stinson | 623/1.16 |
| 2003/0135266 A1 | 7/2003 | Chew et al. | |
| 2003/0144725 A1 | 7/2003 | Lombardi | |
| 2003/0191519 A1 * | 10/2003 | Lombardi et al. | 623/1.13 |
| 2003/0195611 A1 * | 10/2003 | Greenhalgh et al. | 623/1.15 |
| 2003/0211258 A1 | 11/2003 | Sridharan et al. | |
| 2004/0106975 A1 * | 6/2004 | Solovay et al. | 623/1.11 |
| 2005/0027347 A1 * | 2/2005 | Chobotov et al. | 623/1.13 |
| 2005/0173552 A1 * | 8/2005 | Friberg et al. | 239/10 |
| 2007/0088368 A1 * | 4/2007 | Acosta et al. | 606/108 |
| 2007/0208421 A1 | 9/2007 | Quigley | |

FOREIGN PATENT DOCUMENTS

| | | |
|---|---|---|
| GB | 1506432 | 4/1978 |
| GB | 20003387 | 2/2000 |
| JP | 59 062124 | 4/1984 |
| JP | 05-084292 | 4/1993 |
| SU | 468796 | 4/1975 |
| WO | 95/10247 | 4/1995 |
| WO | WO 96/00103 | 1/1996 |
| WO | WO 98/06355 | 2/1998 |
| WO | WO 98/26731 | 6/1998 |
| WO | WO 00/43051 | 7/2000 |

OTHER PUBLICATIONS

PCT International Search Report for International Application No. PCT/US2005/047252, May 17, 2006 (5 pages).

PCT Written Opinion for International Application No. PCT/US2005/047252, May 17, 2006 (8 pages).

U.S. Appl. No. 11/026,777, filed Dec. 31, 2004, Henderson, USPTO Filing Receipt, specification and drawings.

U.S. Appl. No. 11/026,609, filed Dec. 31, 2004, Henderson, USPTO Filing Receipt, specification and drawings.
U.S. Application No. 95/401,871, filed Mar. 10, 1995.

U.S. Appl. No. 95/508,033, filed Jul. 27, 1995.

* cited by examiner

FIG. 11

SINTERED RING SUPPORTED VASCULAR GRAFT

FIELD OF THE INVENTION

The present invention relates generally to a vascular graft formed of polytetrafluoroethylene (PTFE). More specifically, the present invention relates to such a vascular graft having non-expanded and longitudinally expanded portions distributed longitudinally along the graft. Also, the present invention relates to a tubular intermediate from which the vascular graft may be formed, and a method and apparatus for making the vascular graft.

BACKGROUND OF THE INVENTION

It is well known to use extruded tubes of polytetrafluoroethylene (PTFE) as implantable intraluminal prostheses, particularly vascular grafts. PTFE is particularly suitable as an implantable prosthesis as it exhibits superior biocompatibility. PTFE tubes may be used as vascular grafts in the replacement or repair of a blood vessel as PTFE exhibits low thrombogenicity. In vascular applications, the grafts are manufactured from expanded polytetrafluoroethylene (ePTFE) tubes. These tubes have a microporous structure which allows natural tissue ingrowth and cell endothelization once implanted in the vascular system. This contributes to long term healing and patency of the graft. Grafts formed of ePTFE have a fibrous state which is defined by the interspaced nodes interconnected by elongated fibrils.

One disadvantage of current thin-walled or thicker-walled implantable ePTFE tubes is their tendency to kink when subjected to bending forces or concentrated external radial forces. Kinking and luminal constriction can occur during or subsequent to implantation. Such kinking is normally undesirable and poses a risk to the patient.

Accordingly, in applications where kinking is likely, vascular grafts have an additional support structure to prevent kinking. Typically, external support structures, such as helical coils, are bonded around the outer surface of the ePTFE tube. Alternatively, individual rings may be bonded to the outer surface of the ePTFE by injection molding.

Such additional support structures have several disadvantages. For example, the additional support structures are normally bonded to the outer surface of the ePTFE tube thereby increasing the outer diameter of the graft in the regions of the support structures. As a result, implantation of the graft can become more difficult. For example, when tunneling through tissue is required to implant the graft, such as in vascular access applications, a larger cross-sectional tunnel area is required to allow for insertion of the graft.

Another disadvantage of grafts having added support structures is that they are often made from materials which are different from the material of the graft wall and require added processing steps such as heat bonding or additional materials such as adhesive to adhere the support structure to the graft. Differential shrinkage or expansion of the external support structure relative to the ePTFE tube can cause the bond to weaken and/or the graft to twist significantly. Separation of the support structure from the graft is obviously undesirable. Additionally, twisting will normally distort the printed linear guideline which typically runs the length of the ePTFE tube and is used by practitioners to determine proper graft disposition to prevent implantation in a twisted configuration. Such distortion may result in the normally longitudinally linear guideline becoming helical or some other non-linear shape prior to implantation of the vascular graft in the patient, thereby defeating the purpose of the guideline.

Other ePTFE grafts have included external polymeric ribs which provide radial support to the lumen, but increase the outer diameter and wall thickness of the graft.

Thus, there is a need for PTFE tubes which are kink resistant without added support structures such as coils or rings and which do not increase the tube outer diameter.

SUMMARY OF THE INVENTION

The vascular graft of the present invention includes a PTFE tube having non-expanded portions formed from sintering a PTFE green tube extrudate. The non-expanded portions are distributed longitudinally along the PTFE tube. The PTFE tube also has expanded portions formed subsequent to the pre-sintering of the PTFE green tube extrudate. The expanded and non-expanded portions are integral with one another, and alternate with one another along the length of the PTFE tube. The expanded and non-expanded portions each have a respective stiffness, where the stiffness of the non-expanded portions is greater than that of the expanded portions.

The vascular graft has several advantages. The non-expanded portions provide structural support to the PTFE tube to resist kinking thereof. Such structural support is beneficial for thin-walled and thicker-walled PTFE tube, and is especially beneficial for thin-walled PTFE tube. Also, the non-expanded portions do not extend radially beyond the outer surface of the PTFE tube so as to not result in an increase in the outer diameter of the tube in the regions of the non-expanded portions.

Further, the integral relation of the non-expanded portions to the PTFE tube, i.e., the non-expanded portions are part of the PTFE tube which has a uniform material, normally eliminates the possibility of differential shrinkage or expansion of the non-expanded portions relative to the other portions of the PTFE tube. This greatly reduces the possibility of twisting of the PTFE tube, and the associated distortion of the guideline prior to insertion of the graft into the patient, which may result from such twisting. The integral relation of the non-expanded portions to the PTFE tube normally eliminates the possibility of the non-expanded portions becoming detached from the PTFE tube.

The vascular graft may be formed from a tubular intermediate of the present invention. The tubular intermediate includes a PTFE green tube extrudate having sintered portions distributed longitudinally along the extrudate. The extrudate also has un-sintered portions which are integral with the sintered portions, and alternate therewith along the length of the extrudate. The sintered and un-sintered portions each have a respective stiffness, where the stiffness of the sintered portions is greater than that of the un-sintered portions.

An apparatus for making the tubular intermediate of the present invention facilitates formation of the pre-sintered portions thereof.

A method of making the vascular graft of the present invention facilitates the formation of the pre-sintered non-expanded portions and the post-sintered expanded portions of the PTFE tube.

These and other features of the invention will be more fully understood from the following description of specific embodiments of the invention taken together with the accompanying drawings.

BRIEF DESCRIPTION OF THE DRAWINGS

In the drawings.

Corresponding reference characters indicate corresponding parts throughout the several views of the drawings.

DETAILED DESCRIPTION OF THE INVENTION

Figure 1:
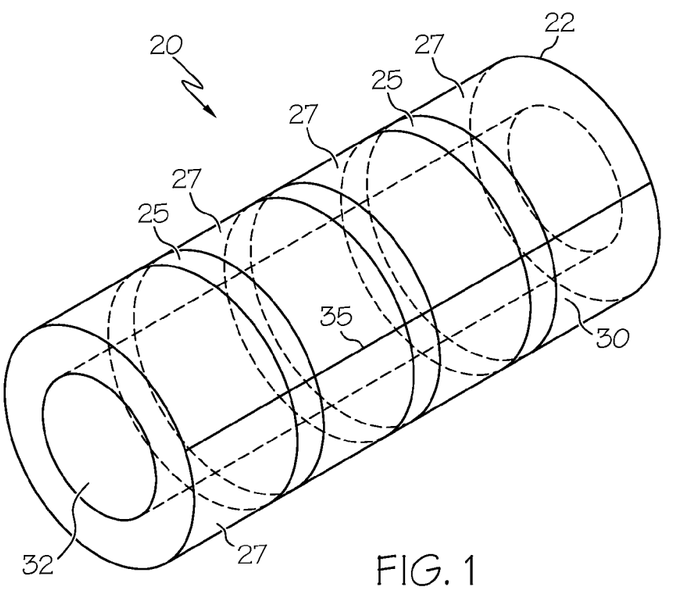
FIG. 1 is a perspective view of the sintered ring supported vascular graft of the present invention, the graft having annular pre-sintered non-expanded portions on the outer surface thereof.
Figure 2:
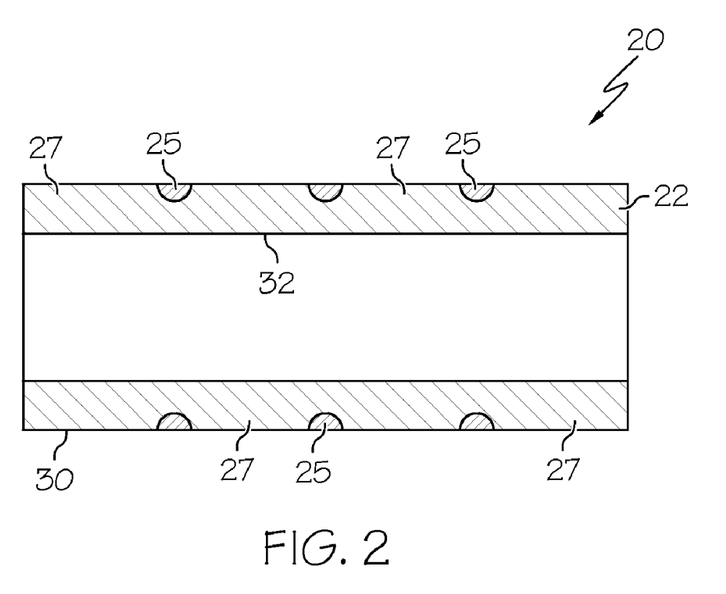
FIG. 2 is a longitudinal cross-sectional view of the graft of FIG. 1.

Referring to the drawings and more particularly to FIGS. 1 and 2, a vascular graft 20 is shown for implantation within a body.

The vascular graft 20 includes a PTFE tube 22 having non-expanded portions 25 formed from sintering a PTFE green tube extrudate. The non-expanded portions 25 have an annular cross-section and are distributed longitudinally along the PTFE tube 22. The PTFE tube 22 also has expanded portions 27 formed subsequent to the sintering of the PTFE green tube extrudate. The expanded portions 27 also have an annular cross-section. The non-expanded and expanded portions 25, 27 are integral with one another, i.e., they are formed from the same extrudate, and alternate with one another along the length of the PTFE tube 22. The non-expanded and expanded portions 25, 27 each have a respective stiffness, where the stiffness of the non-expanded portion is greater than that of the expanded portion. The increased stiffness of the non-expanded portions 25 provide the PTFE tube 22 with a corresponding support characteristic. The support characteristic refers to the magnitude and direction of the resistance to deflection provided by the non-expanded portions 25. The non-expanded portions 25 may provide a support characteristic corresponding to a stent such that the non-expanded portions 25 may possibly provide a substitute for the stent.

The non-expanded portions 25 may extend partially through the PTFE tube 22, as shown in FIG. 2, where the non-expanded portions extend from the outer surface 30 of the PTFE tube 22 radially inward therethrough to a radial position between the outer surface and inner surface 32 of the PTFE tube. This selective sintering partially through the wall thickness can be tuned to provide a structural support and a different structure on the outer surface 30 as compared to the inner surface 32, which remains essentially unchanged.

Alternatively, the non-expanded portions may extend from the inner surface 32 radially outward through the PTFE tube 22 to a radial position between the inner surface and outer surface 30. In another alternative, the non-expanded portions may extend from the outer surface 30 radially inward completely through the PTFE tube 22 to the inner surface 32.

The expanded portions 27 each have a node and fibril structure as a result of expansion. This structure may be locked by sintering the expanded portions 27.

The vascular graft 20 includes a longitudinal guideline 35 printed on the outer surface of each of the expanded portions 27. The longitudinal guidelines 35 on the respective expanded portions 27 are collinear relative to one another.

Figure 3:
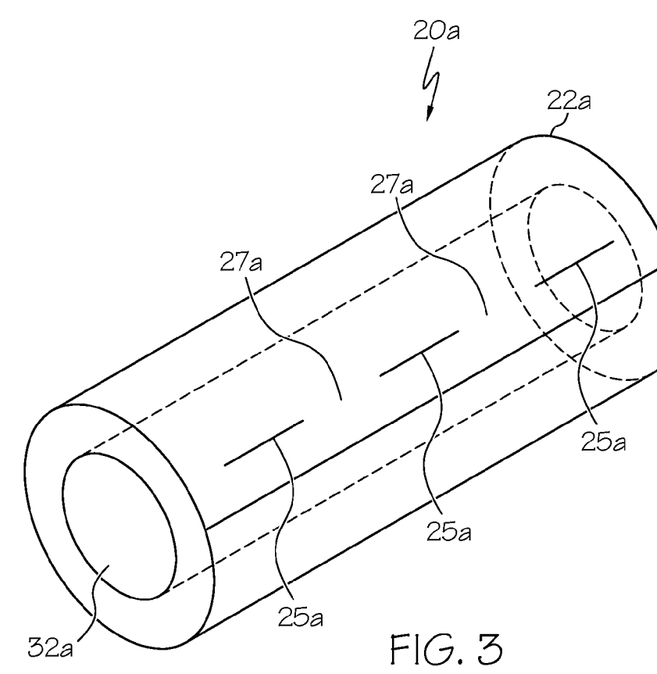
FIG. 3 is a perspective view of the of an alternative embodiment of the vascular graft of FIG. 1, the alternative embodiment having longitudinal pre-sintered non-expanded portions on the outer surface of the graft.

An alternative embodiment for the vascular graft 20a is shown in FIG. 3. Parts illustrated in FIG. 3 which correspond to parts illustrated in FIGS. 1 and 2 have, in FIG. 3, the same reference numeral as in FIGS. 1 and 2 with the addition of the suffix "a". In this alternative embodiment, the PTFE tube 22a has non-expanded portions 25a which are elongate and have a longitudinal axis which is generally parallel to the longitudinal axis of the PTFE tube.

The non-expanded portions 25a may have various lengths and may be arranged in different configurations. Among the possible configurations are the arrangement of the non-expanded portions 25a circumferentially relative to the cross-section of the PTFE tube 22a. Such a configuration may include four non-expanded portions 25a which are parallel to the longitudinal axis of the PTFE tube 22a and which are equally spaced circumferentially to provide for the establishment of quadrants between the non-expanded portions 25a. The non-expanded portions 25a, which define the four quadrants, may have the same or different longitudinal positions relative to the PTFE tube 22a. Additionally, the non-expanded portions 25a may be staggered, both longitudinally and circumferentially, relative to the PTFE tube 22a. Further, the non-expanded portions 25a may be inclined relative to the longitudinal axis of the PTFE tube 22a such as, for example, to provide the non-expanded portions with a helical shape.

The various configurations of the non-expanded portions 25a provide the PTFE tube 22a with corresponding support characteristics. The support characteristic refers to the magnitude and direction of the resistance to deflection provided by the non-expanded portions 25a. The variability of the support characteristic provided by the non-expanded portions 25a facilitates the formation of a PTFE tube 22a having sufficient compliance to a collapsible stent such that the tube remains in close contact with the stent during both collapse and expansion thereof. Collapse of the stent and PTFE tube 22a is typically desired during insertion thereof into a vein or artery. The support characteristic provided by appropriate non-expanded portions 25a may further provide for the radial compression of the PTFE tube 22a, from a circular cross-section to as small as approximately one-half of the diameter thereof, without requiring folding of the PTFE tube. Additionally, the non-expanded portions 25a may be configured to provide a support characteristic corresponding to a stent such that the non-expanded portions 25a may possibly provide a substitute for the stent. Such non-expanded portions 25a which provide the support characteristic of a stent may be further configured to provide for collapse of the PTFE tube 22a for insertion into a vein or artery.

The non-expanded and expanded portions 25, 25a, 27, 27a each have a crystalline structure including highly crystalline polymeric chains. The expanded portions 27 each have a node and fibril structure which results from expansion of PTFE green tube extrudate. The PTFE green tube extrudate has a structure which is essentially continuous node structure. Expansion of the PTFE green tube extrudate fractures the continuous node structure thereof resulting in fibril structures extending between the broken pieces of the remaining node structure, which are the nodes. The respective percentages of the portions of the nodes and fibrils which are crystalline are generally the same. The crystals of the fibrils are more organized than the crystals of the nodes. The nodes of the expanded portions 27, 27a are loosely structured relative to the fibrils. The expanded portions 27, 27a are under a higher stress relative to the stress of the non-expanded portions 25, 25a. The non-expanded portions 25, 25a have a lower energy crystalline structure relative to the energy of the crystalline structure of the expanded portions 27, 27a. This results from the energy of the fibrils of the expanded portions 27, 27a being larger than the energy of the non-expanded portions 25, 25a. When tested with a Differential Scanning Calorimeter (DSC), the expanded portions show a double peak which represents two melting points (Tm). The higher melting point is created from the fibril portion of the microstructure.

The sintering of the PTFE material changes the crystalline structure thereof resulting in the melting temperature of the PTFE material decreasing from approximately 650 degrees F., before the sintering, to approximately 620 degrees F., after the sintering. The non-expanded portions 25, 25a are formed from sintering portions of a PTFE green tube, which is a tube formed of PTFE that has not been sintered or expanded. The PTFE green tube may be formed from a resin, 97% of which may be crystalline, and has a crystalline microstructure. The PTFE green tube may be formed from an extrusion process. The percentage of the expanded portions 27, 27a which have a crystalline microstructure is generally the same as the percentage of the PTFE green tube which has a crystalline microstructure.

Figure 4:
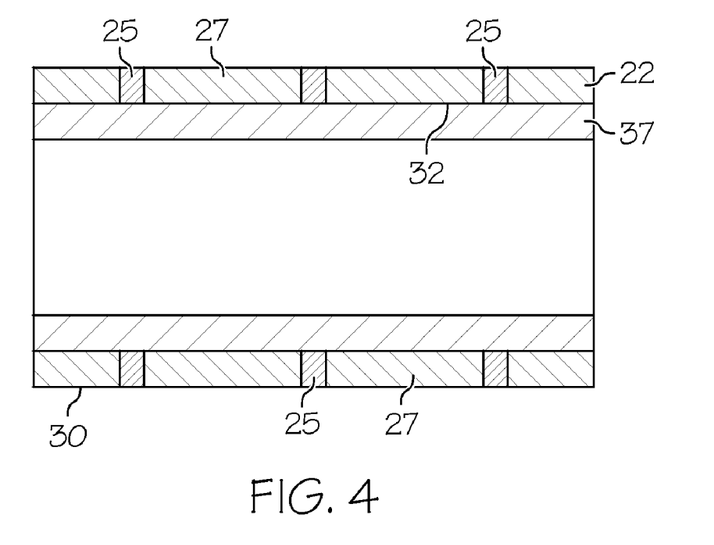
FIG. 4 is a longitudinal cross-sectional view of the graft of FIG. 1 showing a second graft internally of and in coaxial relation with the graft of FIG. 1.

The PTFE tube 22, constituting a stiffened vascular graft, may be used in combination with an additional vascular graft 37, as shown in FIG. 4. In such a combination, the additional vascular graft 37 is disposed within the stiffened vascular graft 20 in coaxial relation thereto. The additional vascular graft 37 includes an expanded PTFE tube which does not necessarily have non-expanded portions, such as are included in the stiffened vascular graft 20. Alternatively, the additional vascular graft 37 may include a tube formed of a textile, such as PTFE, polyester, or other suitable material. The non-expanded portions 25 of the stiffened vascular graft 20 extend from the outer surface 30 radially inward through the PTFE tube 22 to the inner surface 32, as shown in FIG. 4. In this respect, the non-expanded portions 25 shown in FIG. 4 differ from the non-expanded portions 25 shown in FIG. 2. The stiffened and additional vascular grafts 20, 37, if formed of similar materials, are bonded together by polymeric glue or a type of adhesive to maintain the coaxial and relative longitudinal positions of the grafts shown in FIG. 4. Alternatively, it is possible for the stiffened and additional vascular grafts 20, 37, if formed of similar materials, to be sintered together to maintain the coaxial and relative longitudinal positions of the grafts shown in FIG. 4.

In an alternative embodiment, the stiffened vascular graft 20 may be disposed within the additional vascular graft 37 in coaxial relation thereto similar to the orientation shown in FIG. 4. In such an embodiment, the stiffened and additional vascular grafts 20, 37 may have corresponding structures and be bonded or sintered together in a manner similar to that described for the combination shown in FIG. 4.

In a further alternative embodiment, the additional vascular graft 37 may include two or more additional vascular grafts each of which is assembled to the stiffened vascular graft 20 in coaxial relation thereto similar to the orientation shown in FIG. 4. In such an embodiment, the additional vascular graft or grafts may be within or outside of the stiffened vascular graft 20 including an arrangement in which the stiffened vascular graft is radially sandwiched between the separate additional grafts. In such an embodiment, the stiffened vascular graft 20 and each of the additional vascular grafts may have corresponding structures and be sintered together in a manner similar to that described for the combination shown in FIG. 4.

Figure 5:
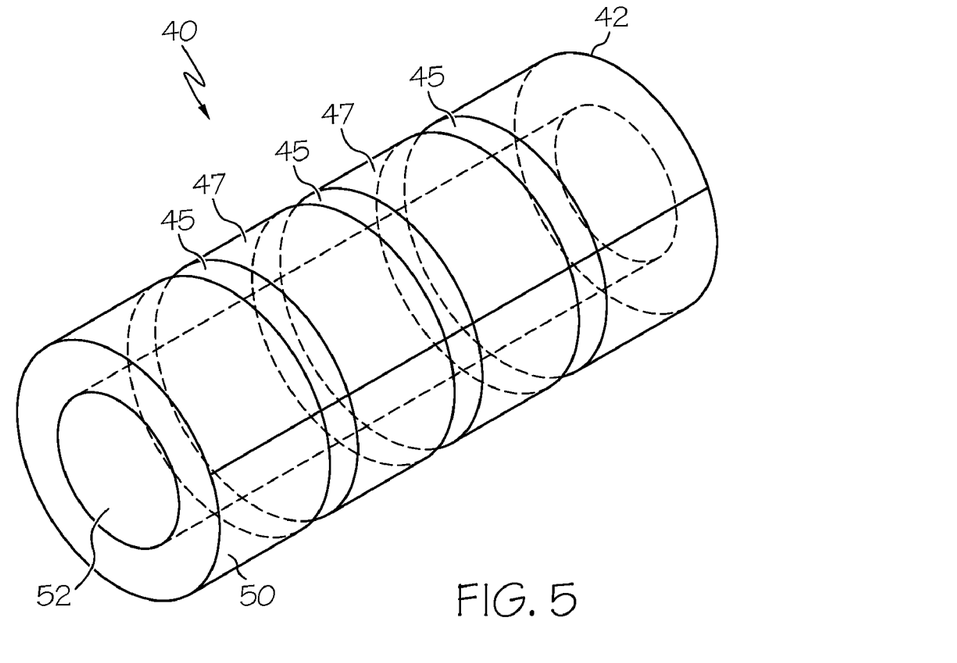
FIG. 5 is a perspective view of the tubular intermediate of the present invention which is expanded to form the graft of FIG. 1.
Figure 6:
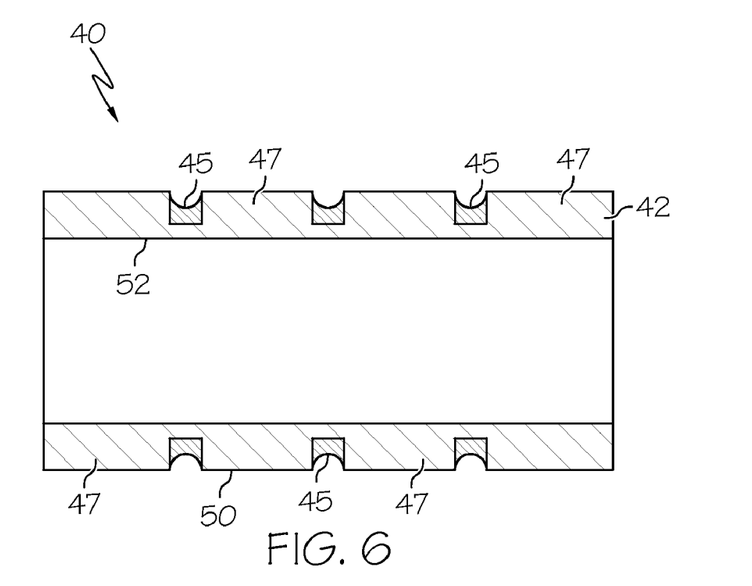
FIG. 6 is a longitudinal cross-sectional view of the intermediate of FIG. 5.

The vascular graft 20 may be formed from a tubular intermediate 40 shown in FIGS. 5 and 6. The tubular intermediate includes a PTFE green tube extrudate 42 having pre-sintered portions 45 distributed longitudinally along the extrudate. The extrudate 42 also has un-sintered portions 47 which are integral with the pre-sintered portions 45, and alternate therewith along the length of the extrudate.

The pre-sintered and un-sintered portions 45, 47 each have an annular cross-section, and a respective stiffness, where the stiffness of the pre-sintered portions is greater than that of the un-sintered portions. The un-sintered portions 47 each have a radial thickness which is constant relative to the longitudinal axis of the extrudate 42. Neither the pre-sintered portion 45 nor the un-sintered portion 47 is expanded. Accordingly, the pre-sintered and un-sintered portions 45, 47 each have crystalline micro-structures which are less organized and at a lower energy state than a typical node and fibril micro-structure which also includes crystalline structure. The respective crystalline micro-structures of the pre-sintered and un-sintered portions 45, 47 are different due to the sintering of the pre-sintered portions 45. This results in the pre-sintered portions 45 being stiffer than the un-sintered portions 47.

The pre-sintered portions 45 may extend radially through the extrudate 42, as shown in FIG. 6, where the pre-sintered portions extend from the outer surface 50 of the extrudate radially inward therethrough to a radial position between the outer surface and inner surface 52. The pre-sintered portions 45 are contiguous with the outer surface 50, and each have an outer diameter which is less than the adjacent regions of the un-sintered portions 47, as shown in FIG. 6.

Alternatively, the pre-sintered portions may extend from the inner surface 52 radially outward through the extrudate 42 to a radial position between the inner surface and outer surface 50. In another alternative, the pre-sintered portions may extend from the outer surface 50 radially inward through the extrudate 42 to the inner surface 52.

Figure 7:
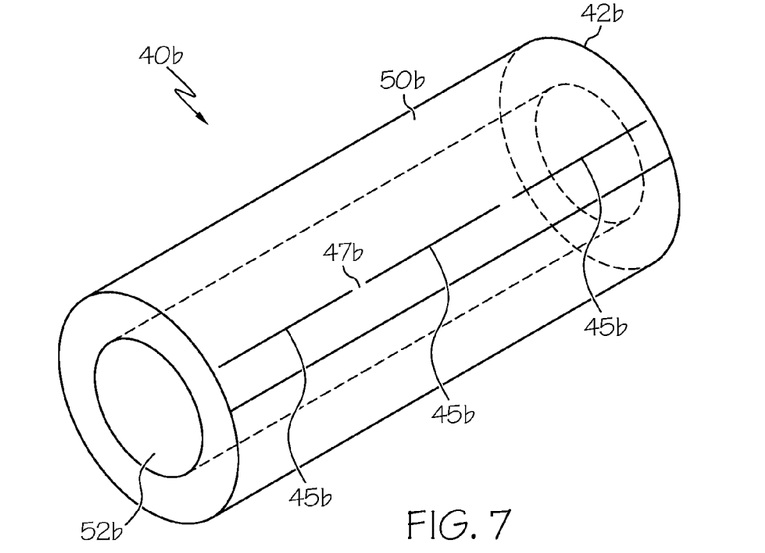
FIG. 7 is a perspective view of an alternative embodiment of the tubular intermediate of FIG. 5, the alternative embodiment having a longitudinal sintered portion on the outer surface of the intermediate.

An alternative embodiment for the tubular intermediate 40b is shown in FIG. 7. Parts illustrated in FIG. 7 which correspond to parts illustrated in FIGS. 5 and 6 have, in FIG. 7, the same reference numeral as in FIGS. 5 and 6 with the addition of the suffix "b". In this alternative embodiment, the extrudate 42a has pre-sintered portions 45a which are elongate and have a longitudinal axis which is generally parallel to the longitudinal axis of the extrudate. The pre-sintered portions 45a may have various lengths and may be arranged in different configurations which provide the corresponding lengths and configurations of the non-expanded portions 25a described in the foregoing.

Figure 8:
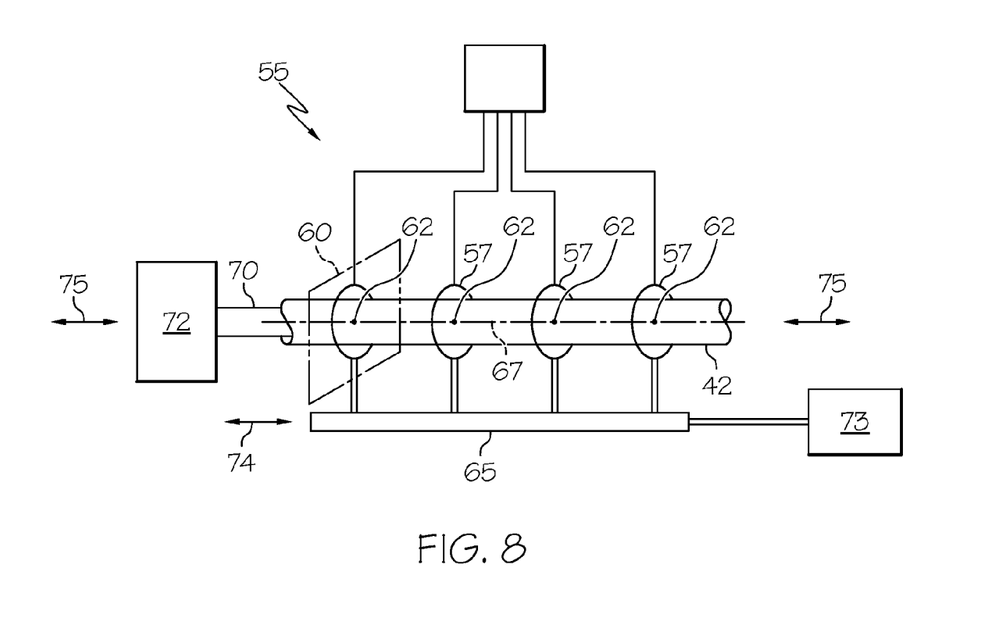
FIG. 8 is a schematic diagram showing an apparatus for making a tubular intermediate of the present invention, the apparatus including a mandrel for supporting a PTFE green tube extrudate, and a plurality of heating filaments encircling the extrudate.

An apparatus 55 for making the tubular intermediate 40 is shown in FIG. 8. The apparatus 55 includes an energy source, such as a plurality of filaments 57, for heating selected portions of the extrudate 42 for sintering thereof. Each filament 57 has a longitudinal central axis which defines a filament axis. Each filament axis is circular and contained in a corresponding filament plane 60. Each of the filaments 57 encircles a filament center 62 which is contained in the corresponding filament plane 60. The apparatus 55 may include alternative energy sources as a means for applying heat to the selected portions of the extrudate 42 for sintering thereof. For example, the selected portions of the extrudate 42 may be heated by a laser, ultrasonics or techniques which provide for localized absorption by the selected portions of sufficient energy to generate the necessary heat for the sintering.

The apparatus 55 includes an elongate fixture 65 on which each of the filaments 57 is mounted such that the filament planes 60 are parallel to one another and the filament centers 62 coincide with an alignment axis 67. Each of the filaments 57 has an inner diameter which is larger than the outer diameter of a corresponding portion of the extrudate 42. This enables the extrudate 42 to be positioned relative to each of the filaments 57 such that each filament encircles the corresponding portion of the extrudate.

The apparatus 55 also includes a support fixture, such as a mandrel 70, for supporting a PTFE green tube extrudate 42. The mandrel 70 is connected to a driver 72 for moving the mandrel to displace the extrudate 42 in the directions indicated by 75 in FIG. 8. The driver 72 may also support the weight of the mandrel 70, although the weight may be supported otherwise. The extrudate 42 is thereby displaced between a position remote from the filaments 57 and a position in sufficient proximity to the filaments to enable the filaments to apply sufficient heat for the sintering of the selected portions of the extrudate.

In an alternative embodiment, the fixture 65 may be connected to a driver 73 for moving the fixture in the directions indicated by 74 in FIG. 8. The fixture 65 may thereby displace the filaments 57 between a position remote from the extrudate 42 and a position in sufficient proximity to the extrudate to enable the filaments to apply sufficient heat for the sintering of the selected portions of the extrudate. The driver 73 may be used instead of, or in combination with, the driver 72, to align the extrudate 42 and filaments 57 relative to each other.

Figure 9:
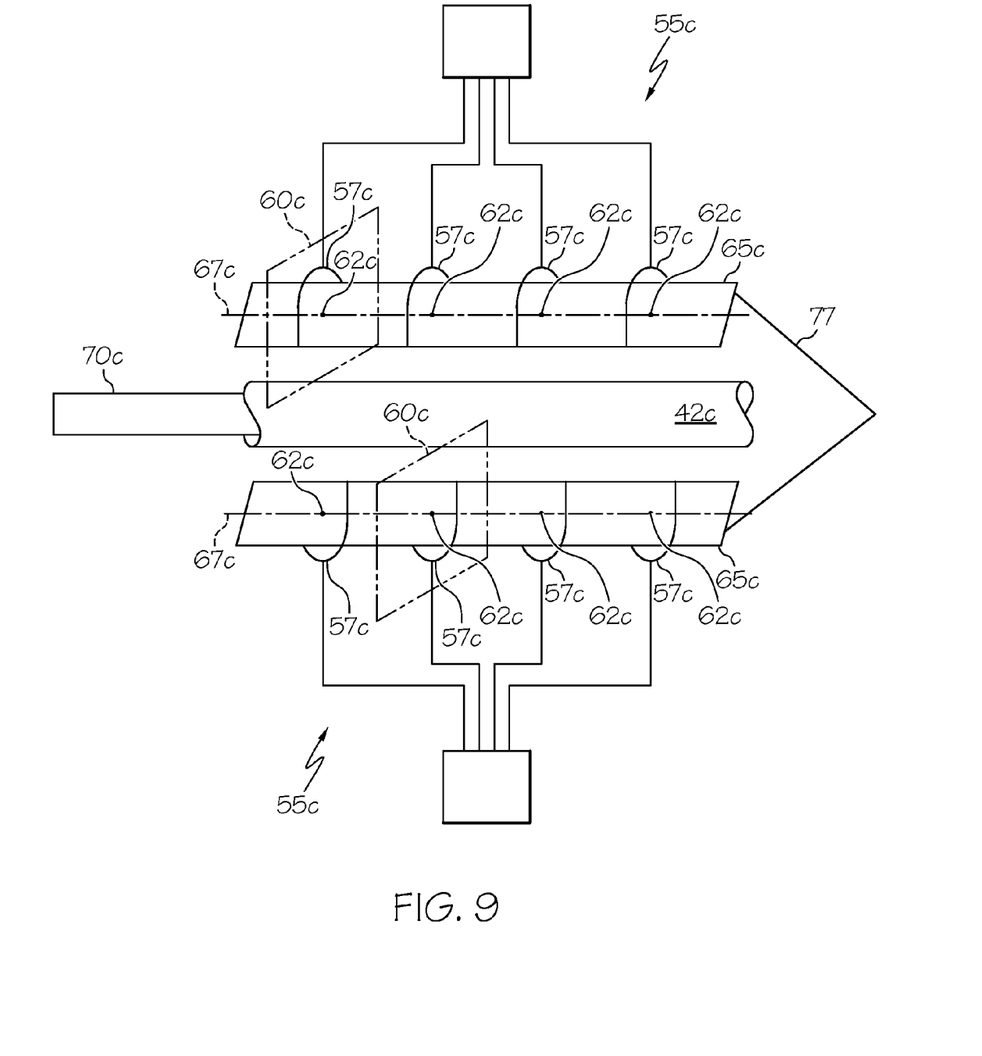
FIG. 9 is a schematic diagram showing an alternative embodiment of the apparatus of FIG. 8, the alternative apparatus including a mandrel for supporting a PTFE green tube extrudate, and a pair of corresponding fixtures on which semi-circular filaments are supported.

An alternative embodiment for the apparatus 55c is shown in FIG. 9. Parts illustrated in FIG. 9 which correspond to parts illustrated in FIG. 8 have, in FIG. 9, the same reference numeral as in FIG. 8 with the addition of the suffix "c". The filaments 57c shown in FIG. 9 each have a longitudinal central axis defining a filament axis which is semi-circular and contained in a corresponding filament plane 60c. Each semi-circular filament 57c partially encircles a filament center 62c which is contained in the corresponding filament plane 60c.

The apparatus 55c has a pair of corresponding elongate fixtures 65c. Each filament 57c is supported on one of the fixtures 65c such that, in each of the fixtures, the filament planes 60c are parallel to one another and the filament centers 62c coincide with a corresponding alignment axis 67c.

Corresponding longitudinal side edges of the fixtures 65c are connected together by a hinge 77 to provide for the fixtures to pivotally open and close in the manner of a clam shell. When the fixtures 65c are pivoted to close them together, the support of the filaments 57c on the fixtures further provides for each of the filaments to mate with a corresponding filament in the other fixture. The mating provides for the corresponding pairs of the filaments 57c to be circular.

Each of the corresponding pairs of filaments 57c have an inner diameter which is larger than the outer diameter of a corresponding portion of the extrudate 42c such that the extrudate can be positioned relative to each of the corresponding pairs such that the corresponding pairs of filaments 57c encircle the corresponding portion of the extrudate.

Figure 10:
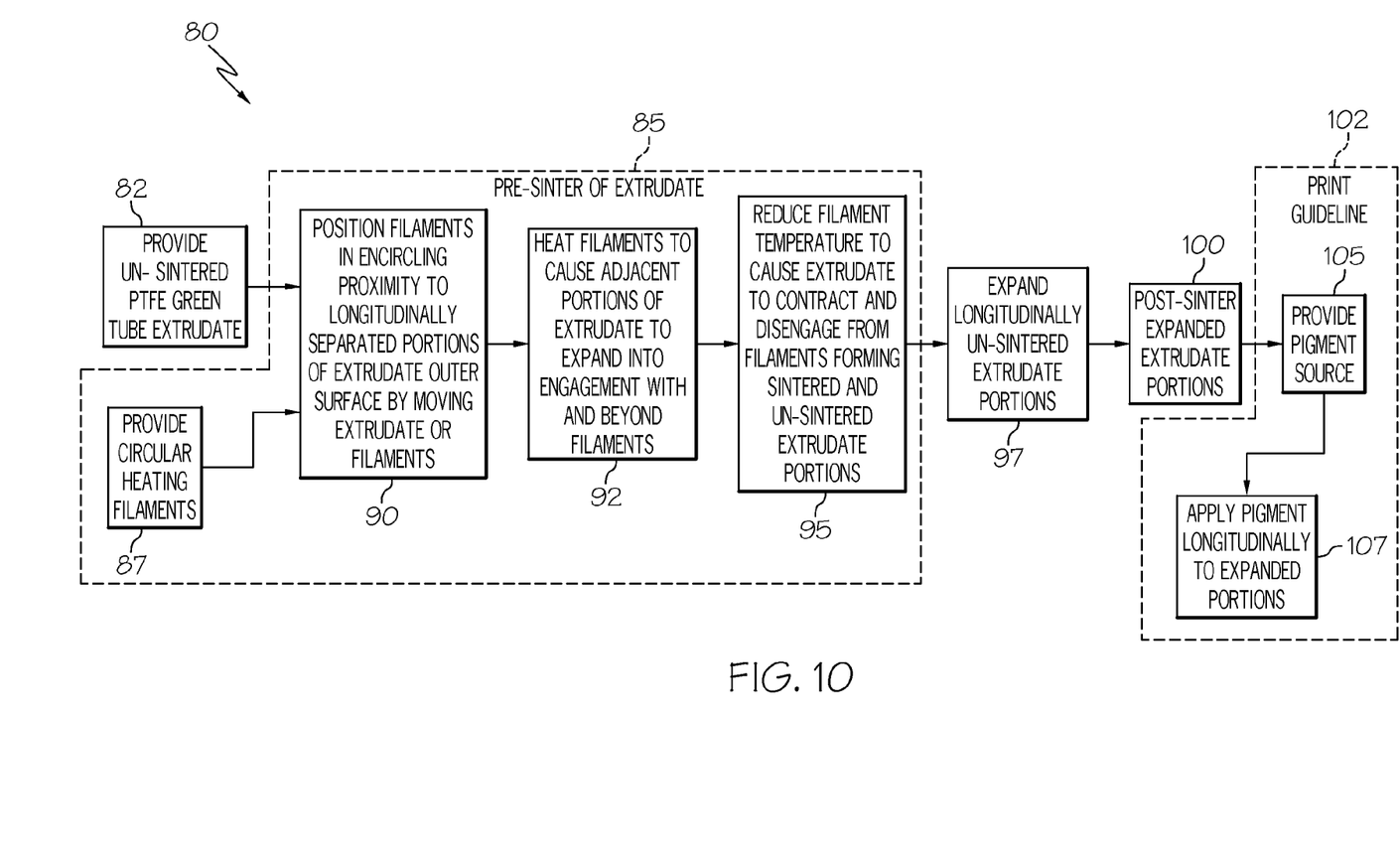
FIG. 10 is a block diagram showing a method for making a vascular graft of the present invention, the method including pre-sintering portions of a PTFE green tube extrudate by using filaments, expanding longitudinally the un-sintered portions of the extrudate, post-sintering the expanded portions of the extrudate, and applying a pigment longitudinally to the expanded portions of the extrudate.

A method for making the vascular graft 20 is shown in the block diagram 80 of FIG. 10. The method 80 includes providing a PTFE green tube extrudate which is un-sintered 82 and a pre-sintering step, designated generally by the reference numeral 85.

The pre-sintering step 85 includes providing a plurality of filaments 87 for heating portions of the extrudate. Such filaments 57, 57c may be provided by the apparatus 55, 55c shown in FIGS. 8 and 9. The filaments 57, 57c are positioned 90 in sufficient proximity to the outer surface of the extrudate 42, 42c to transfer heat thereto. This proximity is provided in the apparatus 55 by the filaments 57 being supported such that the extrudate 42 may be inserted through the circular filaments, or by the filaments being displaced longitudinally so that the extrudate extends therethrough, or by moving both the extrudate and filaments. This proximity is provided in the apparatus 55c by the semicircular filaments 57c being supported on the respective fixtures 65c and the fixtures being connected for closure around the extrudate 42c such that the filaments encircle the extrudate.

The filaments are heated 92 causing portions of the extrudate 42, 42c to expand radially outward into engagement with the filaments 57, 57c, and further causing the portions of the extrudate which are lateral of the filaments to expand radially outward beyond the filaments. The heated filaments 57, 57c thereby sinter portions of the extrudate 42, 42c which become the pre-sintered portions 45. The circular configuration of the filaments 57, 57c and the transfer of heat therefrom to the extrudate 42, 42c results in the pre-sintered portions 45 of the extrudate each having an annular cross-section, as shown in FIG. 5.

The pre-sintering step 85 further includes reducing the temperatures of the filaments 95 to cause the portions of the extrudate 42, 42c expanded by the heating step 92 to contract radially inward such that the extrudate disengages from the filaments 57, 57c resulting in the portions of the extrudate which engaged the filaments having respective outer diameters which are less than the outer diameters of the adjoining portions of the extrudate, as shown in FIG. 6.

The pre-sintering step 85 may limit the sintering of the extrudate 42, 42c such that the pre-sintered portions 45 are contiguous with the outer surface 50 of the extrudate and extend radially therethrough to a radial position between the inner surface 52 and outer surface. Alternatively, using an apparatus which differs from the apparatus 55, 55c, the pre-sintering step 85 may provide for sintering the inner surface 52 of the extrudate 42, 42c such that the pre-sintered portions 45 are contiguous the inner surface of the extrudate and extends radially therethrough to a radial position between the inner surface and outer surface 50.

The pre-sintered portions 45 of the extrudate 42, 42c have a stiffness which is greater than the stiffness of the un-sintered portions 47 of the extrudate.

The method 80 further includes an expanding step 97 following the pre-sintering step 85. The expanding step 97 includes expanding the extrudate 42, 42c longitudinally to reduce the radial thickness of the un-sintered portions 47 of the extrudate, as measured by compression thereof. These reduced thickness portions define the expanded portions 27 of the PTFE tube 22. The expanded portions 27 have a density which is substantially less than the density of the extrudate 42, 42c.

The expanding step 97 provides for the preservation of the structure of the pre-sintered portions 45 such that the structure is substantially the same from just before the expanding step to just after the expanding step. The pre-sintered portions 45 are substantially the same as the non-expanded portions 25 of the PTFE tube 22.

The method 80 includes a post-sintering step 100 following the expanding step 97. In the post-sintering step 100, the expanded portions 27 of the PTFE tube 22 are sintered to lock the structure of the expanded portions. The post-sintering step 100 provides for the preservation of the structure of the pre-sintered portions 45 such that the structure of the pre-sintered portions remains substantially the same from before the post-sintering step to after the post-sintering step.

The method 80 optionally includes a printing step 102 following the post-sintering step 100. The printing step 102 includes providing a source of pigment 105, and applying the pigment 107 to a longitudinal portion of the expanded portions 27 of the PTFE tube 22 such that the pigment affixed to the expanded portions defines the longitudinal guideline 35.

Figure 11:
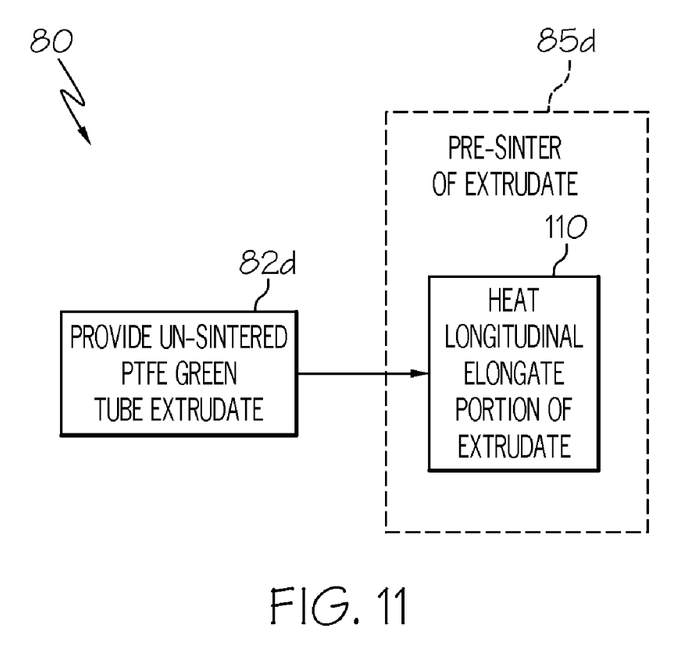
FIG. 11 is a block diagram showing an alternative embodiment of the method of FIG. 10, the alternative embodiment including sintering a longitudinal elongate portion of a PTFE green tube extrudate.

An alternative embodiment of the method 80d is shown in FIG. 11. Steps illustrated in FIG. 11 which correspond to steps in FIG. 10 have, in FIG. 11, the same reference numeral as in FIG. 10 with the addition of the suffix "d". As shown in FIG. 11, the pre-sintering step 85d includes heating 110 an elongate portion of the extrudate 42b such that the pre-sintered portions 45b each have a longitudinal axis which is parallel to the longitudinal axis of the extrudate, as shown in FIG. 7.

The entire disclosures of the following U.S. Patent Applications, each of which is being filed in the USPTO on even date herewith, are hereby incorporated by reference herein:

Title: "Differentially Expanded Vascular Graft"; Inventor: Jamie Henderson; application Ser. No. 11/026,777 and Title: "Sintered Structures for Vascular Graft"; Inventor: Jamie Henderson; application Ser. No. 11/026,748.

While the invention has been described by reference to certain preferred embodiments, it should be understood that numerous changes could be made within the spirit and scope of the inventive concept described. Accordingly, it is intended that the invention not be limited to the disclosed embodiments, but that it have the full scope permitted by the language of the following claims.

What is claimed is:

1. A vascular graft for implantation within a body, said vascular graft comprising
   a monolithic PTFE tube having a length, said monolithic PTFE tube having an inner wall surface and an outer wall surface, said monolithic PTFE tube having a wall structure between said inner wall surface and outer wall surface,
   said monolithic PTFE tube having a pre-sintered non-expanded portion including a non-fibrous microstructure,
   said monolithic PTFE tube having a longitudinally expanded portion including a node and fibril microstructure,
   said expanded portion and said pre-sintered non-expanded portion being of the same extrudate such that said pre-sintered non-expanded portion defines a section of said wall structure,
   said expanded portion and said pre-sintered non-expanded portion each having a respective stiffness, said stiffness of said pre-sintered non-expanded portion being greater than said stiffness of said expanded portion,
   said expanded portion and said pre-sintered non-expanded portion each having a respective outer diameter, said respective outer diameters of said expanded portion and said pre-sintered non-expanded portion being the same.

2. The vascular graft according to claim 1, wherein said pre-sintered non-expanded portion and said expanded portion have respective crystalline structures, said crystalline structure of said expanded portion having a higher energy relative to said crystalline structure of said non-expanded portion.

3. The vascular graft according to claim 1, wherein said pre-sintered non-expanded portion has an annular cross-section.

4. The vascular graft according to claim 1, and further comprising a plurality of said pre-sintered non-expanded portions and said expanded portions alternating along the length of the graft.

5. The vascular graft according to claim 1, and further comprising a longitudinal guideline printed on an outer surface of said expanded portion.

6. A monolithic PTFE tube comprising a first end and a second end defining a length therebetween, said monolithic PTFE tube further comprising an inner wall surface and an outer wall surface, the inner wall surface defining a lumen between said first end and said second end, said monolithic PTFE tube having a wall structure between said inner wall surface and outer wall surface, said monolithic PTFE tube further comprising a plurality of longitudinally expanded portions and pre-sintered non-expanded portions along said length such that said pre-sintered non-expanded portions each define a section of said wall structure, said expanded portions each having a node and fibril microstructure, said pre-sintered non-expanded portions each having a non-fibrous microstructure, said expanded portions and said pre-sintered non-expanded portions each having a respective outer diameter, said respective outer diameters of said expanded portions and said pre-sintered non-expanded portions being the same.

7. The monolithic PTFE tube according to claim 6, wherein said expanded portion and said pre-sintered non-expanded portion have respective crystalline structures, said crystalline structures of said pre-sintered non-expanded portions having lower energies relative to said crystalline structures of said expanded portions.

8. The PTFE tube according to claim 6, and further comprising a longitudinal guideline printed on the outer surface of each of said expanded portions, said longitudinal guidelines being collinear relative to one another.

9. The PTFE tube according to claim 6, wherein said expanded portions are sintered.

10. A tubular intermediate which may be manufactured into a vascular graft for implantation within a body, said tubular intermediate comprising
   a PTFE green tube extrudate having a length and a wall structure including a wall thickness, said PTFE green tube extrudate having an outer surface and an inner surface, said PTFE green tube extrudate having a plurality of pre-sintered unexpanded portions, each portion comprising a non-fibrous microstructure;
   said PTFE green tube extrudate having an un-sintered portion including a continuous node structure, said pre-sintered unexpanded portions extending from one of said outer or inner surfaces into said wall structure such that said pre-sintered unexpanded portions have a thickness which is smaller than said wall thickness of said wall structure, each of said pre-sintered unexpanded portions defining a section of said wall structure, each of said pre-sintered unexpanded portions having respective longitudinal positions relative to said PTFE green tube extrudate which are different from one another, said pre-sintered unexpanded portions and said un-sintered portion each having a respective stiffness, said stiffness of said pre-sintered unexpanded portions being greater than said stiffness of said un-sintered portion;

said plurality of pre-sintered unexpanded portions being parallel to the longitudinal axis of said PTFE green tube extrudate and extending along at least a portion of said length, said plurality of pre-sintered unexpanded portions being spaced circumferentially to define four quadrants.

11. The tubular intermediate according to claim 10, wherein said pre-sintered unexpanded portions and said un-sintered portion have respective crystalline structures, said crystalline structure of said pre-sintered unexpanded portions having a lower energy relative to said crystalline structure of said un-sintered portion.

12. The tubular intermediate according to claim 10, wherein said pre-sintered unexpanded portions are distributed longitudinally between a plurality of said un-sintered portions, said pre-sintered unexpanded portions each extending from one of said outer or inner surfaces into said wall structure such that said pre-sintered unexpanded portions each have a thickness which is smaller than said wall thickness of said wall structure, said pre-sintered unexpanded portions each defining a section of said wall structure, said pre-sintered unexpanded portions each having a non-fibrous microstructure, said un-sintered portions each having a continuous node structure, said pre-sintered unexpanded portions and said un-sintered portions each having a respective stiffness, said stiffnesses of said pre-sintered unexpanded portions being greater than said stiffnesses of said un-sintered portions.

* * * * *